United States Patent
Keyvani et al.

(10) Patent No.: US 10,343,959 B2
(45) Date of Patent: Jul. 9, 2019

(54) PARAFFIN REMOVAL FROM C4 CONTAINING STREAMS

(71) Applicant: Lyondell Chemical Technology, L.P., Houston, TX (US)

(72) Inventors: Majid Keyvani, Houston, TX (US); Gary A. Sawyer, Media, PA (US); Arsam Behkish, Flemington, NJ (US)

(73) Assignee: Lyondell Chemical Technology, L.P., Houston, TX (US)

( * ) Notice: Subject to any disclaimer, the term of this patent is extended or adjusted under 35 U.S.C. 154(b) by 50 days.

(21) Appl. No.: 15/660,535

(22) Filed: Jul. 26, 2017

(65) Prior Publication Data
US 2018/0029958 A1    Feb. 1, 2018

Related U.S. Application Data

(60) Provisional application No. 62/367,914, filed on Jul. 28, 2016.

(51) Int. Cl.
| | |
|---|---|
| *C07C 7/08* | (2006.01) |
| *C07C 5/22* | (2006.01) |
| *C07C 9/10* | (2006.01) |
| *C07C 11/08* | (2006.01) |

(Continued)

(52) U.S. Cl.
CPC .................. *C07C 7/08* (2013.01); *B01D 3/40* (2013.01); *B01D 53/22* (2013.01); *C07C 5/222* (2013.01); *C07C 5/2213* (2013.01); *C07C 7/144* (2013.01); *C07C 9/10* (2013.01); *C07C 11/08* (2013.01); *C07C 41/06* (2013.01); *C07C 255/03* (2013.01);

(Continued)

(58) Field of Classification Search
CPC .... C07C 5/22; C07C 7/08; C07C 9/10; C07C 9/22; C07C 11/08; C10G 7/08; C10G 21/12; C10G 45/58; C10G 45/60; C10G 67/02; C10G 70/045; C10G 70/048
See application file for complete search history.

(56) References Cited

U.S. PATENT DOCUMENTS

| | | | |
|---|---|---|---|
| 2,921,103 A | 1/1960 | Pitzer | |
| 4,513,153 A * | 4/1985 | Sandrin | C07C 7/08 568/697 |

(Continued)

FOREIGN PATENT DOCUMENTS

| | | |
|---|---|---|
| WO | 2014074261 A1 | 5/2014 |
| WO | 2015009969 A1 | 1/2015 |
| WO | 2015170282 A1 | 11/2015 |

OTHER PUBLICATIONS

The International Search Report and Written Opinion for PCT/US2017/043972 dated Oct. 23, 2017.

*Primary Examiner* — Brian A McCaig

(57) ABSTRACT

The present disclosure relates to processes for the removal of paraffins. The processes generally include providing a $C_4$ containing stream including isobutylene, 1-butene, 2-butene, n-butane and isobutane, introducing the $C_4$ containing stream into a paraffin removal process to form an olefin rich stream, wherein the paraffin removal process is selected from extractive distillation utilizing a solvent including an organonitrile, passing the $C_4$ containing stream over a semi-permeable membrane and combinations thereof; and recovering the olefin rich stream from the paraffin removal process, wherein the olefin rich stream includes less than 5 wt. % paraffins.

18 Claims, 2 Drawing Sheets

(51) Int. Cl.
*C10G 21/12* (2006.01)
*C10G 45/58* (2006.01)
*B01D 3/40* (2006.01)
*C07C 255/03* (2006.01)
*B01D 53/22* (2006.01)
*C07C 41/06* (2006.01)
*C07C 7/144* (2006.01)
*C10G 21/16* (2006.01)
*C10G 29/20* (2006.01)
*C10G 31/00* (2006.01)
*C10G 45/60* (2006.01)
*C10G 57/00* (2006.01)
*C10G 67/02* (2006.01)
*C10G 67/04* (2006.01)
*C10G 70/04* (2006.01)
*C10G 7/08* (2006.01)
*C07C 9/22* (2006.01)

(52) U.S. Cl.
CPC ............... *C10G 7/08* (2013.01); *C10G 21/12* (2013.01); *C10G 21/16* (2013.01); *C10G 29/205* (2013.01); *C10G 31/00* (2013.01); *C10G 45/58* (2013.01); *C10G 45/60* (2013.01); *C10G 57/005* (2013.01); *C10G 67/02* (2013.01); *C10G 67/0409* (2013.01); *C10G 70/045* (2013.01); *C10G 70/048* (2013.01); *C07C 9/22* (2013.01)

(56) References Cited

U.S. PATENT DOCUMENTS

| | | | |
|---|---|---|---|
| 4,814,542 A * | 3/1989 | Forlani | B01J 23/02 585/666 |
| 6,706,771 B2 * | 3/2004 | Kim | B01D 53/228 210/638 |
| 2005/0154246 A1 | 7/2005 | Adrian et al. | |
| 2006/0021911 A1 * | 2/2006 | Adrian | B01D 3/141 208/115 |
| 2006/0047176 A1 * | 3/2006 | Gartside | C07C 5/2506 585/643 |
| 2014/0124358 A1 | 5/2014 | Schwint et al. | |
| 2015/0025293 A1 | 1/2015 | Feiring et al. | |
| 2017/0073289 A1 | 3/2017 | Leal et al. | |

* cited by examiner

PARAFFIN REMOVAL FROM C4 CONTAINING STREAMS

CROSS-REFERENCE TO RELATED APPLICATIONS

This application claims the benefit of priority to U.S. Provisional Application No. 62/367,914, filed on Jul. 28, 2016, which is incorporated herein by reference in its entirety.

BACKGROUND OF THE INVENTION

The present disclosure generally relates to processes for removing paraffins from $C_4$ containing streams. Particular embodiments described herein relate to 1-butene production processes.

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Steam cracker crude $C_4$ streams contain a mixture of saturates (e.g., n-butane, isobutane), olefins (1-butene, 2-butene and isobutene) and diolefins (primarily butadiene). The 1-butene is a valuable co-monomer in many polyethylene formulations. However the components from the crude $C_4$ streams are not conveniently separated by conventional distillation.

The present disclosure is directed to resolving, or at least reducing, one or all of the problems mentioned above.

SUMMARY OF THE INVENTION

Various embodiments of the present disclosure include 1-butene production processes. The processes generally include introducing a $C_4$ containing stream into a paraffin removal process to form an olefin rich stream, wherein the paraffin removal process is selected from: (a) extractive distillation utilizing a solvent comprising an organonitrile; (b) passing the $C_4$ containing stream over a semi-permeable membrane; and (c) combinations thereof; and isomerizing at least a portion of the 2-butene present in the olefin rich stream to 1-butene to form an isomerization product stream including at least 80 wt. % 1-butene, including at least 95 wt. % 1-butene.

One or more embodiments include the processes of the preceding paragraph, wherein the $C_4$ containing stream includes raffinate-1.

One or more embodiments include the processes of any preceding paragraph, wherein the $C_4$ containing stream includes isobutylene, 1-butene, 2-butene, n-butane and isobutane.

One or more embodiments include the processes of any preceding paragraph, wherein the $C_4$ containing stream includes 1-butene, 2-butene, n-butane and isobutane.

One or more embodiments include the processes of any preceding paragraph, wherein the $C_4$ containing stream includes paraffins and olefins.

One or more embodiments include the processes of any preceding paragraph, wherein the $C_4$ containing stream includes from 40 wt. % to 70 wt. % olefins and from 30 wt. % to 85 wt. % paraffins.

One or more embodiments include the processes of any preceding paragraph, wherein the solvent includes acetonitrile.

One or more embodiments include the processes of any preceding paragraph, wherein the solvent is characterized by a relative volatility of $C_4$ over solvent of at least 1.70.

One or more embodiments include the processes of any preceding paragraph, wherein the solvent is diluted with water prior to extractive distillation.

One or more embodiments include the processes of any preceding paragraph, wherein the solvent is diluted with an amount of water sufficient to provide a solvent mixture including from 1 wt. % to 15 wt. % water.

One or more embodiments include the processes of any preceding paragraph, wherein the semi-permeable membrane includes a polysaccharide membrane chelated with a metal selected from silver, copper and combinations thereof.

One or more embodiments include the processes of any preceding paragraph, wherein the semi-permeable membrane is chelated with from 30 wt. % to 60 wt. % metal.

One or more embodiments include the processes of any preceding paragraph, wherein the olefin rich stream includes less than 5 wt. % paraffins.

One or more embodiments include the processes of any preceding paragraph further including separating 1-butene present in the olefin rich stream prior to isomerizing.

One or more embodiments include the processes of any preceding paragraph, wherein the isomerization product stream comprises at least 95 wt. % 1-butene.

One or more embodiments include the processes of any preceding paragraph, wherein the isomerizing at least a portion of the 2-butene present in the butene stream to 1-butene occurs in the presence of an isomerization catalyst including a potassium promoted alpha aluminum catalyst.

One or more embodiments include the processes of any preceding paragraph, wherein the isomerizing at least a portion of the 2-butene present in the butene stream to 1-butene occurs at isomerization conditions including a temperature of at least 350° C., a WHSV ("weight hourly space velocity") of at least 10 $hr^{-1}$, and a pressure of from 75 psig to 125 psig.

One or more embodiments include MTBE production processes including providing a $C_4$ containing stream, wherein the $C_4$ containing stream includes less than 5 wt. % paraffins; contacting the $C_4$ containing stream with methanol in the presence of an ion-exchange catalyst to produce an MTBE effluent stream including methyl-tertiary-butyl-ether (MTBE); and recovering MTBE from the MTBE production process.

One or more embodiments include processes for the removal of paraffins. The processes generally include providing a $C_4$ containing stream including isobutylene, 1-butene, 2-butene, n-butane and isobutane: introducing the $C_4$ containing stream into a paraffin removal process to form an olefin rich stream, wherein the paraffin removal process is selected from extractive distillation utilizing a solvent comprising an organonitrile, passing the $C_4$ containing stream over a semi-permeable membrane and combinations thereof; and recovering the olefin rich stream from the paraffin removal process, wherein the olefin rich stream includes less than 5 wt. % paraffins.

One or more embodiments include the process of the preceding paragraph, wherein the olefin rich stream is introduced into an alkylation process, an olefin conversion process, an isomerization process, an MTBE production process or combinations thereof.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

Figure 1:
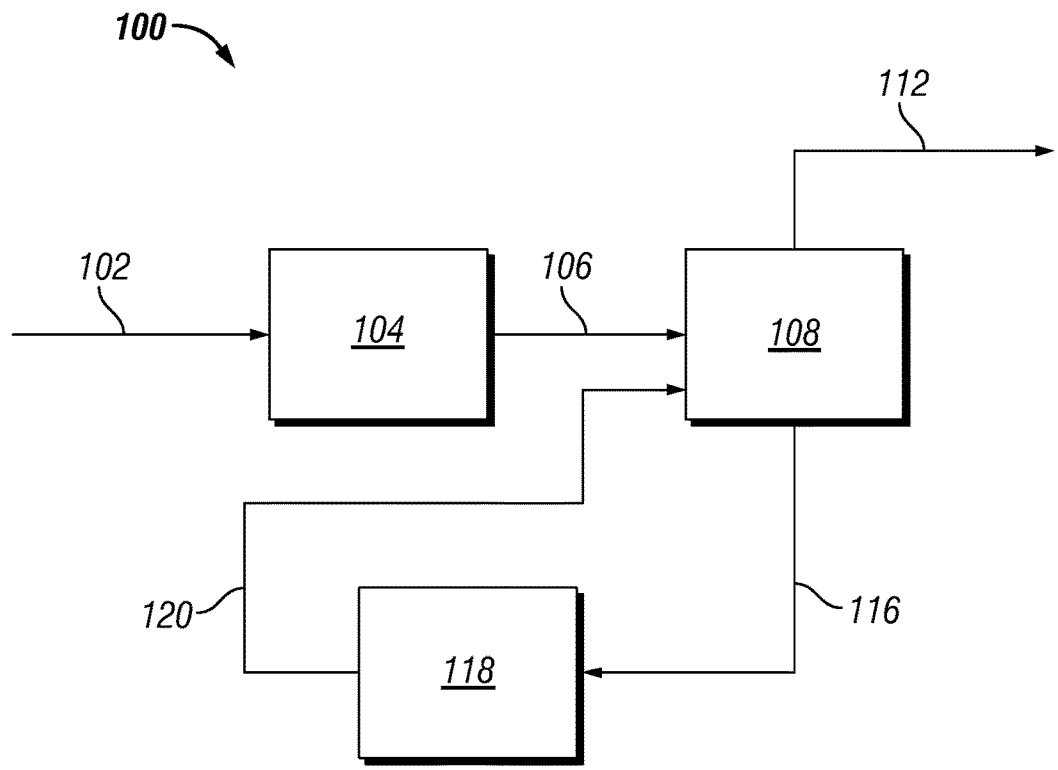
FIG. 1 illustrates a schematic of one or more embodiments of the disclosed process.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope of the disclosure as defined by the appended claims.

DETAILED DESCRIPTION OF THE INVENTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein include processes for removing paraffins from $C_4$ containing streams. For illustrative purposes, the removal of paraffins is discussed herein with reference to specific 1-butene production processes. However, it is contemplated that any portion of the process discussed herein may be utilized as a standalone process or within another process, without limitation. For example, the resultant olefin rich stream (discussed in further detail below) may be utilized in alkylation processes or olefin conversion processes.

One or more embodiments described herein include 1-butene production processes. 1-butene (often referred to as B-1) is a favored co-monomer in the production of linear low-density and high-density polyethylene. B-1 is also used as a building block in the production of plasticizers as well as the manufacture of high performance gasoline additives, for example. Specific, non-limiting embodiments of such 1-butene production processes are described below.

In one or more embodiments, the 1-butene production processes include paraffin removal. The paraffin removal generally includes processes for removing paraffins from a $C_4$ containing stream, thereby forming an olefin rich stream. The $C_4$ containing stream may include a crude $C_4$ stream, for example. Crude $C_4$ streams often include a variety of components, including, but not limited to, butadiene, isobutylene, 1-butene, 2-butene, n-butane and isobutane, for example. Crude $C_4$ streams may be sourced from a variety of processes, including steam cracking processes, for example. The relative proportions of the various components within the crude $C_4$ stream will depend upon the source and the feedstocks utilized to produce such source.

Alternatively, or in combination with the crude $C_4$ stream, the $C_4$ containing stream may include a raffinate-1 stream. The remaining stream upon separation of the butadiene from the crude $C_4$ stream is often referred to as raffinate-1. As described previously herein, the raffinate-1 stream may include olefins (e.g., 1-butene and 2-butene) and paraffins (e.g., n-butane, i-butane and isobutylene), as well as other components, for example. Accordingly, the raffinate-1 stream may alternatively be referred to as a mixed butylene stream. It is generally recognized in the art that olefins can also be referred to as alkenes. However, for clarity herein, such compounds will be referred to as olefins throughout this specification. Furthermore, paraffins, which can also be referred to as alkanes, will be referred to as paraffins throughout this specification.

In one or more embodiments, the $C_4$ containing stream may include from 20 wt. % to about 90 wt. %, or from 30 wt. % to 85 wt. % or from 40 wt. % to 70 wt. % olefins and from 20 wt. % to about 90 wt. %, or from 30 wt. % to 85 wt. % or from 40 wt. % to 70 wt. % paraffins, for example.

In one or more embodiments, the $C_4$ containing stream is processed to remove the paraffins therefrom, thereby forming the olefin rich stream. In one or more embodiments, the paraffins are removed from the $C_4$ containing stream via extractive distillation.

As known in the art, extractive distillation processes are distillation processes utilizing a solvent. The solvent is generally a miscible compound that forms no azeotrope with other components in the $C_4$ containing stream. As used herein, the extractive distillation processes, including the solvent, are adapted to separate the paraffins from the olefins in the $C_4$ containing stream. In one or more embodiments, the solvent is an organonitrile, such as acetonitrile or benzonitrile, for example. In one or more specific embodiments, the organonitrile is at least slightly soluble in water but is immiscible with paraffins. In one or more specific embodiments, the solvent is acetonitrile.

The selection of an appropriate extractive distillation solvent is important for accomplishing the distillation separation of closely boiling materials. The solvent must be capable of enhancing the relative volatility of one component with respect to the other component in order that the separation be accomplished and also the solvent must be readily separable from the component with which is becomes associated. Although there are a great number of materials which have in the past been separated by extractive distillation procedures, the art at best is an empirical one and it is not feasible to ascertain in advance which solvents would accomplish a desired separation. However, it has been determined that the solvents utilized within embodiments of the disclosure can be characterized by their relative volatility. Relative volatility is a ratio of the K value for one component to that of another. K values, also known as equilibrium ratios or distribution coefficients, are ratios of the mole fraction in one phase to that in a different phase, and are functions of temperature and pressure (and composition as well in non-ideal systems). For vapor-liquid systems it is the ratio in the vapor phase to that in the liquid phase. The K value, in a binary mixture, is determined by obtaining experimental vapor-liquid equilibrium for the desired components. In one or more embodiments, the solvent is characterized by a relative volatility of $C_4$ over solvent of at least 1.65 or at least 1.70, for example.

Embodiments may further include diluting the solvent with water. Such dilution has been proven to improve (i.e., increase) the relative volatility of the solvent (or solvent mixture). In one or more embodiments, the solvent may be diluted with water to provide a solvent mixture having from 1 wt. % to 15 wt. %, or from 2 wt. % to 10 wt. %, or from 5 wt. % to 8 wt. % water, for example. As described previously herein, the solvent or solvent mixture may be characterized by a relative volatility of $C_4$ over solvent of at least 1.65 or at least 1.70, for example. For example, one or more embodiments include diluting the solvent with water in an amount to provide a mixed solvent having the designated relative volatility.

In practice, extractive distillation conditions vary depending upon numerous factors. However, in one or more embodiments, the extractive distillation may occur at a pressure of from 50 psig to 100 psig, or from 60 psig to 90 psig, for example and a temperature of from 25° C. to 100° C., or from 30° C. to 90° C. or from 40° C. to 60° C., for example.

In one or more embodiments, the paraffin removal includes passing the $C_4$ containing stream over a semi-permeable membrane. The olefins preferentially pass through the semi-permeable membrane, resulting in a permeate stream and a retentate stream. The permeate stream is richer in olefins and the retentate stream is richer in paraffins.

The selectivity of the membrane is such that under the conditions of use, not less than 80 wt. %, or not less than 90 wt. %, or not less than 95 wt. %, or not less than 98 wt. % of the olefins in the $C_4$ containing stream pass through the membrane.

The membrane may be supported. The support may be formed from one or more compounds selected from polyesters, polyamides, polyimides, polyacrylonitrile, polysulphones, polycarbonates and combinations thereof, for example. The support may be in the form of a film of fibers, for example and may have a thickness of from 20 microns to 200 microns, or from 50 microns to 150 microns, for example. Methods for forming such compounds into the membrane are known to one skilled in the art.

In one or more embodiments, the membrane is a polysaccharide membrane which has been chelated with a metal selected from silver, copper and combinations thereof. The membrane may be chelated with from 30 wt. % to 60 wt. %, or from 45 wt. % to 55 wt. % on a dry basis of the metal based on the total weight of the membrane, for example.

Examples of polysaccharides for use in the membrane include natural polysaccharides, such as alginic acid, pectic acid, chondroitin, hyaluronic acid and xanthan gum, cellulose, chitin, pullulan, derivatives, such as $C_1$ to $C_6$, or $C_1$ to $C_4$, esters, ether and alkylcarboxy derivatives thereof and phosphates of these natural polysaccharide such as partially methylesterified alginic acid, carbomethoxylated alginic acid, phosphorylated alginic acid and aminated alginic acid, salts of anionic cellulose derivatives, such as carboxymethyl cellulose, cellulose sulfate, cellulose phosphate, sulfoethyl cellulose and phosphonoethyl cellulose, and semi-synthetic polysaccharides such as guar gum phosphate and chitin phosphate, for example. Specific examples of membranes of polysaccharides include those composed of salts of chitosan and its derivatives such as N-acylated chitosan, chitosan phosphate and carbomethoxylated chitosan. Of these, membranes composed of alginic acid, and salts and derivatives thereof, chitosan and salts and derivatives thereof cellulose and derivatives thereof (other than the mono-, di-, and tri-acetate derivatives thereof which are not intended to be included in the present disclosure) are utilized in one or more specific embodiments. The membrane may also include membranes composed of blends of a major amount (e.g., at least 60 wt. %) of the polysaccharides and lesser amounts (e.g., up to 40 wt. %) of other compatible polymeric substances, such as polyvinyl alcohol (PVA) or neutral polysaccharides, such as starch and pullulan, and membranes composed of grafted ionized polysaccharides obtained by grafting a hydrophilic vinyl monomer such as acrylic acid, for example.

The $C_4$ containing stream may be passed over the membrane at conditions sufficient to remove at least a portion of the paraffins therefrom. For example, the conditions may include a pressure from 10 psig to 75 psig, or from 20 psig to 50 psig, for example and a temperature of from 20° C. to 60° C., or from 30° C. to 50° C. for example.

Whether via extractive distillation, passing over the membrane or a combination thereof, upon paraffin removal, the olefin rich stream may have less than 10 wt. %, or less than 5 wt. %, or less than 3 wt. %, or less than 2 wt. % or less than 1 wt. % paraffins, for example.

It is contemplated that the olefin rich stream (or any other stream within the overall 1-butene production process) may be further processed to separate the components thereof. For example, the olefin rich stream may undergo separation to separate the 1-butene from any remaining components, thereby forming a butene stream. The separation processes may include those known in the art, such as fractionation. As used herein, the term "fractionation" refers to processes for the separation of components based on the relative volatility and/or boiling point of the components. The fractionation processes may include those known in the art and the term "fractionation" can be used interchangeably with the terms "distillation" and "fractional distillation" herein.

The butene stream (or in alternative embodiments, the olefin rich stream) may be further processed to isomerize the remaining components (e.g., 2-butene) to form 1-butene. Accordingly, the isomerization reaction includes contacting the butene stream with an isomerization catalyst to convert the 2-butene present in the butene stream to 1-butene, thereby forming an isomerization product stream rich in butene-1. For example, the isomerization product stream may include at least 85 wt. %, or at least 90 wt. %, or at least 95 wt. %, or at least 98 wt. % 1-butene.

The isomerization catalyst generally includes any isomerization catalyst capable of converting 2-butene to 1-butene. For example, the isomerization catalyst may include zeolites, metal oxides, mixed metal oxides and combinations thereof, for example. In one or more embodiments, the isomerization catalyst includes a basic double-bond isomerization catalyst, such as a metal oxide (e.g., magnesium oxide, tungsten oxide, calcium oxide, barium oxide, lithium oxide and combinations thereof). Metal oxides supported on a carrier may be used. Suitable carriers include silica, alumina, titanic, silica-alumina and combinations thereof, for example.

In one or more specific embodiments, the isomerization catalyst includes a potassium promoted alpha aluminum catalyst. For example, the isomerization catalyst may include a potassium promoted alumina formed into a tri-lobe shape having a diameter of from 0.5 mm to 0.95 mm and a length of from 2.75 mm to 3.75 mm. The isomerization catalyst may exhibit a crush strength of from 6 lb-force to 9 lb-force, for example. One or more specific embodiments utilize SBC-1, commercially available from CRI Catalyst Company, as the isomerization catalyst.

The isomerization reaction may occur at conditions sufficient to convert at least a portion of the 2-butene present to 1-butene. For example, the isomerization may occur at an isomerization temperature of at least 350° C., or at least 360° C., or at least 380° C., a WHSV of at least 10 $hr^{-1}$, or at least 12 $hr^{-1}$, or at least 15 $hr^{-1}$ and a pressure of from 50 psig to 150 psig, or from 75 psig to 125 psig, or from 90 psig to 110 psig.

In one or more embodiments, the olefin rich stream may be further processed to remove the isobutylene therefrom and thereby form an MTBE effluent stream. This can be accomplished in a MTBE production process by reaction with methanol to produce methyl-tertiary-butyl-ether (MTBE). MTBE is produced by reacting isobutylene with methanol in the presence of a catalyst. The reaction typically is conducted in the liquid phase and under relatively mild conditions. The catalyst utilized can be those known in the art, such as an ion-exchange resin, for example.

In one or more embodiments, the MTBE production process may occur at a pressure sufficient to maintain the reactants in liquid phase from 30 psig to 300 psig) and a temperature of from 15° C. to 150° C., or from 50° C. to 100° C., for example.

The MTBE production process generally forms an MTBE effluent stream including isobutane, normal butane, straight chain butenes, a small amount of unreacted isobutylene, a small amount of unreacted methanol, and MTBE, for example. The MTBE production process may further include separation processes as known in the art. For example, the MTBE effluent stream may undergo separation to remove MTBE forming an effluent stream including butenes and unreacted methanol. The unreacted methanol may be removed from the effluent stream via methods known in the art, such as adsorption, for example. Adsorption may be carried out with any absorbent suitable for the retention of methanol such as alumina, silica gel, molecular sieve, ion-exchange resin, or other materials well known in the art. Adsorption is carried out under conditions which are suitable to effect removal of methanol from the butenes and may include temperatures of from 10° C. to 100° C. and pressures of from 50 psig to 300 psig, for example. The time required for adsorption will depend on the amount and type of adsorbent used and the operating conditions employed, but may vary between 2 and 12 hours, for example.

Separation of the MTBE and the unreacted methanol from the MTBE effluent stream results may result in a stream having a composition such as that referenced as the butene stream previously herein.

It is further contemplated that additional processes, such as impurities removal, may be included within the 1-butene production process. For example, the 1-butene production process may include optional pre-treatment of the butene stream with a molecular sieve or other process known to remove impurities, such as sulfur and/or water therefrom.

FIG. 1 illustrates a simplified, non-limiting, process scheme that may be utilized for a 1-butene production process 100. As depicted, process flow lines in the figures can be referred to as lines, pipes or streams. Particularly, a line or a pipe can contain one or more streams, and one or more streams can be contained by a line or a pipe.

The 1-butene production process 100 generally includes providing a $C_4$ containing stream 102 to a paraffin removal process 104 adapted to remove paraffins from the $C_4$ containing stream 102, thereby forming an olefin rich stream 106. The olefin rich stream 106 may be passed to a separation process 108 for 1-butene removal. 1-butene is separated from the remaining components within the separation process 108 and the separated 1-butene is then removed from the separation process 108 via line 112, while the remaining components are recovered from the separation process 108 via butene stream 116.

Butene stream 116 may be passed through an isomerization process 118 to isomerize at least a portion of the 2-butene present in the butene stream 116 to 1-butene, which can then be recovered from the isomerization process 118 via the isomerization product stream 120 (which is illustrated in FIG. 1 as being recycled to separation system 108 for 1-butene separation and continuous recycle of the unreacted 2-butene to the isomerization process 118).

Figure 2:
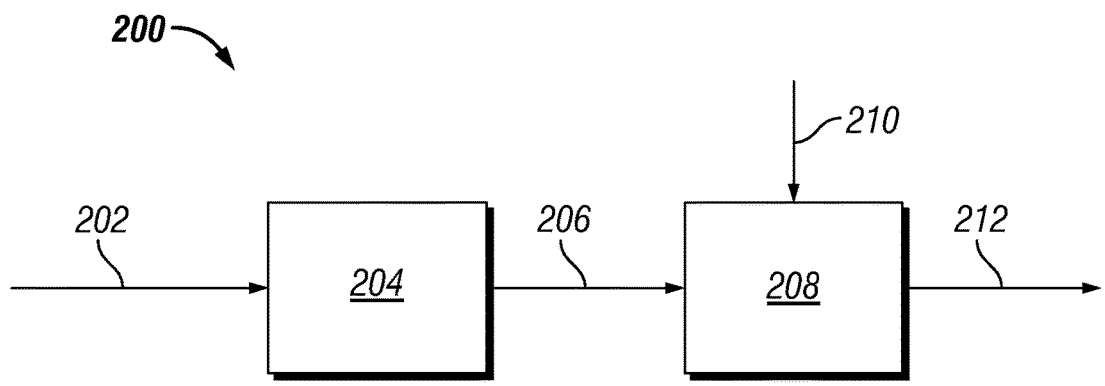
FIG. 2 illustrates a schematic of alternative embodiments of the disclosed process.

FIG. 2 illustrates an alternative process scheme that may be utilized for an MTBE production process 200. As depicted, process flow lines in the figures can be referred to as lines, pipes or streams. Particularly, a line or a pipe can contain one or more streams, and one or more streams can be contained by a line or a pipe.

The MTBE production process 200 generally includes providing a $C_4$ containing stream 202 to a paraffin removal process 204 adapted to remove paraffins from the $C_4$ containing stream 202, thereby forming an olefin rich stream 206. The olefin rich stream 206 is generally passed to an MTBE process 208 for isobutylene removal. Methanol is generally introduced into the MTBE process 208 via line 210. The olefin rich stream 206 generally contacts a catalyst (not shown) disposed within the MTBE process 208 in the presence of the methanol to form an MTBE effluent stream 212.

EXAMPLES

To facilitate a better understanding of the disclosure, the following examples of embodiments are given. In no way should the following examples be read to limit, or to define, the scope of the appended claims.

Example 1

Extractive distillation was utilized to separate paraffins from olefins and the results were observed to determine whether extractive distillation achieved significant separation. Utilizing acetonitrile as the solvent, 10 lb/hr of a mixed $C_4$ stream (66 wt. % olefins: butenes, and 34 wt. % paraffins: n-butane and iso-butane) was fed to a distillation column with 45 stages. Operating the column at 90 psia and 125° F. condenser temperature, 100 lb/hr of acetonitrile was also fed to the column maintaining a reboiler temperature of 229° F.

It was observed that the process resulted in an olefin free stream in the overhead of the column at a rate of 3.4 lb/hr. Subsequently, the bottoms stream was fed to a second distillation column having 17 stages which was operated at 80 psia and 120° F. condenser temperature. The overhead product from the second column was a paraffin free olefin stream at a rate of 6.6 lb/hr. The acetonitrile solvent was recovered in the bottoms stream of the second column at a rate of 100 lb/hr.

Example 2

Figure 3:
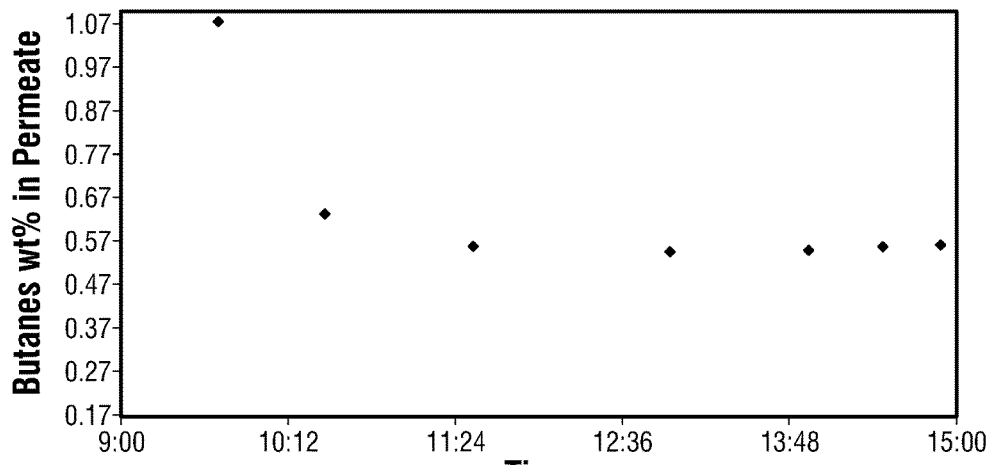
FIG. 3 illustrates a permeate butane concentration over time.

A second process scheme utilizing a membrane to separate paraffins from olefins was undertaken and the results were observed. A mixed $C_4$ stream (73 wt. % $C_4$ olefins and 27 wt. % paraffins) was fed to a 600 $cm^2$ membrane unit (commercially available from Imtex Membrane Corporation) operating at 25 psig and room temperature (about 20-25° C.). The temperature range may be from about room temperature to about 110° F. A total paraffin concentration of 0.57 wt. % was measured in the permeate stream as illustrated in FIG. 3.

Example 3

Figure 4:
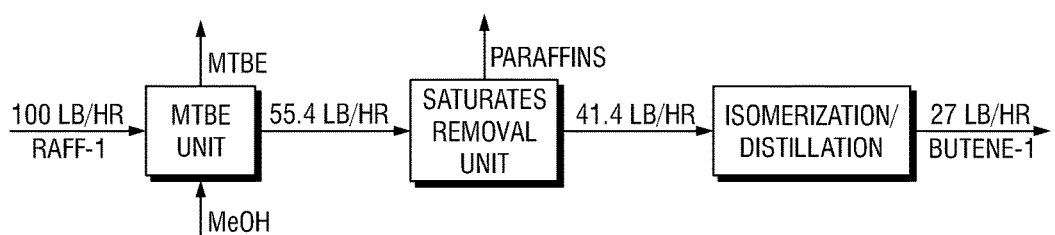
FIG. 4 illustrates a schematic of an MTBE process with paraffin extraction.

Butene-1 was recovered from a raffinate-1 stream according to the process scheme illustrated in FIG. 4. The raffinate-1 stream included 5 wt. % isobutane, 44.6 wt. % isobutylene, 27.4 wt. % butene-1, 8.1 wt. % n-butane, and 14.9 wt. % butene-2. The raffinate-1 stream was fed to an MTBE process unit for reaction with MeOH in the presence of Amberlyst catalyst at a temperature of 100-115° F. and a MeOH/Isobutylene molar ratio of 1.0-1.1 and a liquid space velocity of 3-5 $hr^{-1}$. The stream leaving the MTBE unit included 9.0 wt. % isobutene, 0.10 wt. % isobutylene, 49.3 wt. % 1-butene, 14.6 wt. % n-butane, and 26.8 wt. % 2-butene. The MTBE reaction exhibited 99% conversion to MTBE.

The stream leaving the MTBE unit was passed to a saturates removal process to remove the paraffinic components (n-butane and isobutane) from the olefins (butene-1, butene-2 and isobutylene). The saturate removal process may include a solvent extraction unit or a membrane unit capable of recovering 98% of the incoming olefins while removing all the paraffins from the feed streams. The operating conditions for either unit are those such as described in the prior examples. Regardless of which inventive process was used (the process of example 1 or 2), simulations show that the product stream would include 0 wt. % isobutane, 1300 ppm isobutylene, 65 wt. % butene-1, 0 wt. % n-butane and 35 wt. % butene-2.

The resulting butene stream was passed to a distillation column to separate butene-1 from butene-2. The bottom stream from the distillation column, containing 97 wt. % butene-2 and 3 wt. % butene-1 was passed to an isomerization unit operating at 800° F. to convert butene-2 to butene-1. The stream coming off of the isomerization was also passed to the same distillation column to recover butene-1. The results are illustrated in Table 1 below.

TABLE 1

| | 1<br>Feed<br>Wt. % | 2<br>Reactor Out<br>Wt. % | 3<br>B1<br>Wt. % | 4<br>Recycle<br>Wt. % | 5<br>Heavy Purge<br>Wt. % |
|---|---|---|---|---|---|
| Isobutane | | | | | |
| Isobutylene | 0.001 | 0.000128712 | 0.0005 | 0.000129 | 1.5083E−05 |
| Butene-1 | 0.65 | 0.256008975 | 0.9945 | 0.03 | 0.03 |
| 1,3-butadiene | 0 | 0 | 0 | 0 | 0 |
| n-butane | 0 | 0 | 0 | 0 | 0 |
| Butene-2 | 0.35 | 0.416514789 | 0.0028 | 0.97 | 0.54312882 |

Example 4 (Comparative)

Examples 4 and 5 demonstrate the effect of saturate removal from a raffinate stream on an olefin conversion process. 100 lb/hr of Raff II stream (Raff-I stream depleted of isobutylene after an MTBE process) containing 21 wt. % saturates (isobutane and n-butane), 79 wt. % butenes was fed into a Metathesis process to react with 18 lb/hr of ethylene. The process exhibited a reaction product yield of 59 lb/hr of propylene, 6 lb/hr of gasoline and 53 lb/hr of unreacted Raff-II.

Example 5

The 122 lb/hr Raff-II stream from Example 4 was first sent to a "saturate removal" process (membrane or extractive distillation). All the saturate was removed from the stream and, with 98% olefin recovery, 100 lb/hr of a butenes stream was fed to the same metathesis reactor process as in Example 4 to react with 30 lb/hr of ethylene to produce 98 lb/hr of propylene and 9.9 lb/hr of gasoline.

Example C-E

Figure 5:
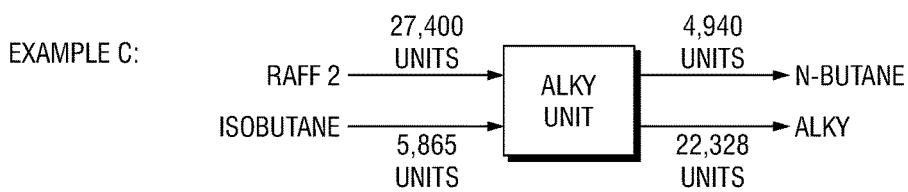
FIG. 5 illustrates a schematic of an alkylation process.
Figure 5:
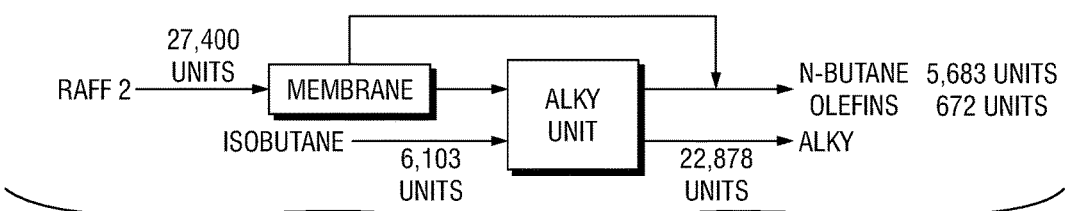

Examples 6-8 demonstrate debottleneck capability of saturate removal for Alkylation processes. For example, example D showed 550 units improvement for Alkyl production with the membrane olefin recovery of 89%. See FIG. 5.

Example E is repeat of Example D with 94% olefin recovery for membrane which resulted in 1600 units improvement in Alkyl production.

While the foregoing is directed to embodiments of the present disclosure, other and further embodiments of the disclosure may be devised without departing from the basic scope thereof and the scope thereof is determined by the claims that follow.

What is claimed is:

1. A 1-butene production process comprising:
   introducing a $C_4$ containing stream into a paraffin removal process to form an olefin rich stream, wherein the paraffin removal process comprises the step:
   (a) extractive distillation utilizing a solvent comprising an organonitrile; and
   (b) optionally, passing the $C_4$ containing stream over a semi-permeable membrane; and
   wherein the solvent is diluted with water prior to extractive distillation with an amount of water sufficient to provide a solvent mixture comprising from 1 wt. % to 15 wt. % water; and
   isomerizing at least a portion of the 2-butene present in the olefin rich stream to 1-butene to form an isomerization product stream comprising at least 80 wt. % 1-butene wherein the isomerizing at least a portion of the 2-butene present in the olefin rich stream to 1-butene occurs in the presence of an isomerization catalyst comprising a potassium promoted alpha aluminum catalyst.

2. The process of claim 1, wherein the C4 containing stream comprises raffinate-1.

3. The process of claim 1, wherein the C4 containing stream comprises isobutylene, 1-butene, 2-butene, n-butane and isobutane.

4. The process of claim 1, wherein the C4 containing stream comprises paraffins and olefins.

5. The process of claim 1, wherein the C4 containing stream comprises from 20 wt. % to 70 wt. % olefins and from 30 wt. % to 80 wt. % paraffins.

6. The process of claim 1, wherein the solvent comprises acetonitrile.

7. The process of claim 1, wherein the solvent is diluted with water prior to extractive distillation with an amount of water sufficient to provide a solvent mixture comprising from 2 wt. % to 10 wt. % water.

8. The process of claim 1, wherein the paraffin removal process comprises passing the C4 containing stream over a semi-permeable membrane comprising 30-60 wt. % metal selected from silver, copper and combinations thereof and a polysaccharide membrane chelated with the metal.

9. The process of claim 1, wherein the olefin rich stream comprises less than 5 wt. % paraffins.

10. The process of claim 1 further comprising separating 1-butene present in the olefin rich stream prior to isomerizing.

11. The process of claim 1, wherein the isomerization product stream comprises at least 95 wt. % 1-butene.

12. The process of claim 1, wherein the isomerizing at least a portion of the 2-butene present in the olefin rich stream to 1-butene occurs at isomerization conditions comprising a temperature of at least 350° C., a WHSV of at least 10 hr$^{-1}$, and a pressure of from 75 psig to 125 psig.

13. The process of claim 1 further comprising separating isobutylene present in the olefin rich stream prior to isomerizing.

14. The process of claim 13, wherein the separating isobutylene comprises contacting the olefin rich stream with methanol in the presence of an ion-exchange catalyst.

15. A process for the removal of paraffins:
providing a $C_4$ containing stream comprising isobutylene, 1-butene, 2-butene, n-butane and isobutane:
introducing the $C_4$ containing stream into a paraffin removal process to form an olefin rich stream, wherein the paraffin removal process comprises the step of extractive distillation utilizing a solvent comprising an organonitrile, wherein the solvent is diluted with water prior to extractive distillation with an amount of water sufficient to provide a solvent mixture comprising from 1 wt. % to 15 wt. % water; and recovering the olefin rich stream from the paraffin removal process, wherein the olefin rich stream comprises less than 5 wt. % paraffins
wherein the olefin rich stream is introduced into an isomerization process, and the isomerization process comprises isomerizing at least a portion of the 2-butene present in the olefin rich stream to 1-butene in the presence of an isomerization catalyst comprising a potassium promoted alpha aluminum catalyst.

16. The process of claim 15, wherein the olefin rich stream is introduced into a alkylation process, an olefin conversion process, an isomerization process, an MTBE production process or combinations thereof.

17. The process of claim 15, wherein the isomerizing at least a portion of the 2-butene present in the olefin rich stream to 1-butene occurs at isomerization conditions comprising a temperature of at least 350° C., a WHSV of at least 10 hr$^{-1}$, and a pressure of from 75 psig to 125 psig.

18. The process of claim 15, comprising the step of passing the C4 containing stream over a semi-permeable membrane.

* * * * *